United States Patent
Dick et al.

(10) Patent No.: US 11,353,382 B2
(45) Date of Patent: Jun. 7, 2022

(54) PLASMA SEPARATION CARD

(71) Applicant: Roche Molecular Systems, Inc., Pleasanton, CA (US)

(72) Inventors: Siegfried Dick, Mannheim (DE); Markus Fischer, Moerlenbach (DE); Alexander Schmelzer, Mannheim (DE); Andreas Trapp, Lampertheim (DE); Stephen G. Will, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 16/843,130

(22) Filed: Apr. 8, 2020

(65) Prior Publication Data

US 2020/0232892 A1 Jul. 23, 2020

Related U.S. Application Data

(62) Division of application No. 15/085,882, filed on Mar. 30, 2016, now Pat. No. 10,663,379.

(60) Provisional application No. 62/141,089, filed on Mar. 31, 2015.

(30) Foreign Application Priority Data

Feb. 11, 2016 (EP) .................................. 16155284

(51) Int. Cl.
| G01N 1/00 | (2006.01) |
| G01N 1/40 | (2006.01) |
| G01N 33/52 | (2006.01) |
| G01N 33/49 | (2006.01) |
| C12Q 1/70 | (2006.01) |

(52) U.S. Cl.
CPC ............ *G01N 1/405* (2013.01); *C12Q 1/703* (2013.01); *G01N 33/491* (2013.01); *G01N 33/525* (2013.01); *G01N 2001/4088* (2013.01)

(58) Field of Classification Search
CPC ................... G01N 33/56983; G01N 2800/52
USPC ................... 436/177, 178, 174, 506
See application file for complete search history.

(56) References Cited

U.S. PATENT DOCUMENTS

| 5,516,487 A | 5/1996 | Rosenthal et al. |
| 5,552,276 A | 9/1996 | Mochida et al. |
| 5,948,687 A | 9/1999 | Cleator |
| 6,106,732 A * | 8/2000 | Johnston ............... B01L 3/5023 210/503 |
| 2006/0063267 A1 | 3/2006 | Lawrence et al. |
| 2006/0188392 A1 | 8/2006 | Tanaka et al. |
| 2012/0037513 A1 | 2/2012 | Lindemann |
| 2012/0088227 A1 | 4/2012 | Gruebl et al. |
| 2017/0318802 A1 | 11/2017 | Hopper |

FOREIGN PATENT DOCUMENTS

| WO | 95/35497 A1 | 12/1995 |
| WO | 98/01753 A1 | 1/1998 |
| WO | 2015/022410 A1 | 2/2015 |
| WO | 2016/025726 A1 | 2/2016 |

OTHER PUBLICATIONS

International Bureau, on behalf of the International Searching Authority, "International Preliminary Report on Patentability" for International Patent Application No. PCT/EP2016/056888 (dated Oct. 3, 2017).
International Searching Authority, "International Search Report" for International Patent Application No. PCT/EP2016/056888 (dated Oct. 6, 2016).
International Searching Authority, "Written Opinion of the International Searching Authority" for International Patent Application No. PCT/EP2016/056888 (dated Oct. 6, 2016).

* cited by examiner

*Primary Examiner* — Natalia Levkovich
(74) *Attorney, Agent, or Firm* — Eric Grant Lee

(57) ABSTRACT

A multi-layer plasma separation card comprising (a) a first layer including a sample receiving member comprising (i) a top planar surface for applying or receiving a blood sample, said sample receiving portion being adapted to permit contact of said blood sample with a separating member; and (ii) a bottom planar surface being adapted to contact said separating member, (b) a second layer including at least three separating members, each separating member being adapted to permit the passage of plasma to an absorptive member and comprising (i) a top planar surface for receiving said blood sample; and (ii) a bottom planar shield-shaped surface being adapted to contact said absorptive member, and (c) a third layer including at least two absorptive members for absorbing plasma from the bottom planar surface of each corresponding separating member and a backing member arranged in a manner to support said absorptive members, each absorptive member comprising a removable absorptive element having a top planar surface being adapted to contact said bottom planar surface of the separating member, said absorptive element is detachable fixed to the third layer.

12 Claims, 12 Drawing Sheets

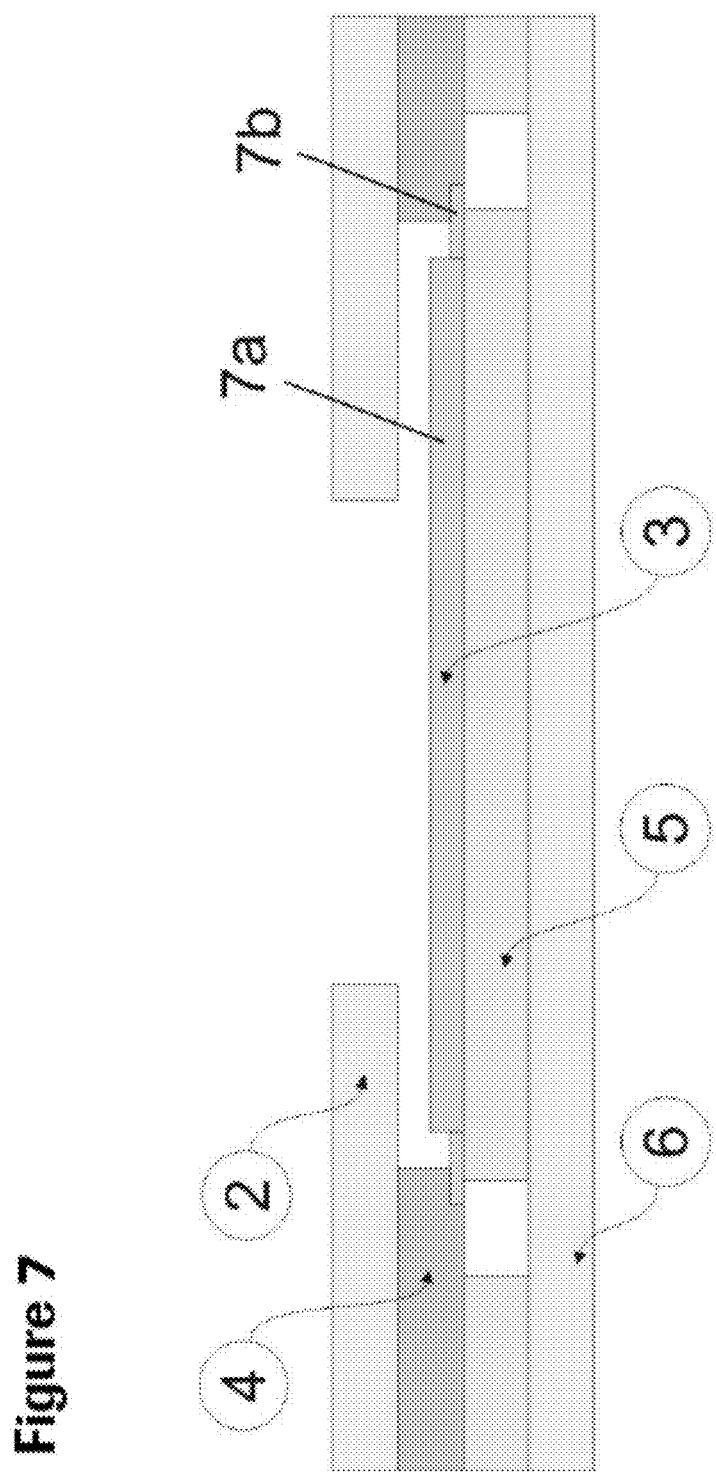

PLASMA SEPARATION CARD

CROSS-REFERENCE TO RELATED APPLICATIONS

The present application is a continuation patent application of U.S. patent application Ser. No. 15/085,882, filed Mar. 30, 2016, now U.S. Pat. No. 10,663,379, granted May 26, 2020, which claims priority to U.S. Provisional Application No. 62/141,089, filed Mar. 31, 2015, and EP Application No. 16155284, filed Feb. 11, 2016, the disclosures of which are incorporated herein by reference in their entireties.

FIELD OF THE INVENTION

The present invention relates to the field of sample collection devices.

BACKGROUND OF THE INVENTION

Blood analysis is commonly carried out on a sample of whole blood which, for the majority of tests, is drawn from the vein of the arm, the finger or the earlobe. A number of tests and procedures have been developed and many can be carried out simultaneously on one blood sample with such instruments as automatic analyzers. While most hematological tests relate to the blood cells, in modern routine diagnostic testing, many tests are done on plasma or serum instead of the blood cells. Specifically, in recent years, an increasing number of immunochemical and nucleic acid analysis items have been developed. For instance, special tests can be used to detect substances contained in the plasma which are characteristic of specific infections such as HIV (Human Immunodeficiency Virus) particles.

In 2013, the World Health Organization (WHO) revised the current HIV treatment and prevention guidelines and emphasized the importance of HIV viral load (VL) testing in the management of HIV positive patients. Recently, WHO strongly recommends using HIV viral load testing to monitor the therapeutic efficacy of HIV Antiretroviral Therapy (ART) and also reduced the cutoff of the level of HIV plasma VL from 5000 copies/ml to 1000 copies/ml. In other words, if HIV patients under ART have a viral titer in plasma is greater than 1000 copies/ml, it will be considered as a drug treatment failure. Responses to treatment failure, such as adherence counseling, drug resistance testing and second line treatment regimens, are time-consuming and expensive, and should be used only if necessary. HIV viral load is normally measured using plasma as a specimen type. However, in resource limited settings, such as Africa, plasma samples may not be easily obtained, stored, transferred, and tested. Dried blood spots (DBS) have been evaluated as a solution for HIV viral load testing in the resource limited settings, with limited success. After infection, HIV virus not only starts to replicate itself in the infected cells, but also integrates its cDNA into the host chromosomes as the latent HIV proviral DNA (Greene, W. C. Peterlin, B. M. 2002. Nat Med. 8(7): 673-80). This additional cellular associated HIV Nucleic Acid can confound the determination of the VL of HIV when whole blood is used as the input sample material leading to unreliable determinations of treatment failure.

Accordingly, in view of performing such tests, there is an increasing need to separate plasma from the whole blood sample. Since these tests often involve sophisticated instruments, shipping of the plasma to specific analysis sites can be required. The European patent EP 1096254 B1 describes a device for separating hematocrit from a whole blood sample provided with an inlet port for receiving the sample, a reaction region and a capillary pathway connecting the inlet port with the reaction region. The capillary pathway which is provided with obstructions for keeping the blood cells back is integrally formed with the reaction region. U.S. Published Patent Application No. 2012/0088227 describes a device for separating plasma from a blood sample using a stacked structure having separating and absorptive members. The devices comprising a separation membrane and a plasma collection pad described by McClernon and McClernon (20$^{th}$ Annual DART Conference, Maui/Hawaii, USA, Dec. 6-10, 2015) are easier to handle, however, there is still a risk of cross-contamination when removing the plasma collection pad. Further, it is required that the plasma collection or adsorbent pad can be easily removed from the device and, moreover, that the plasma sample is sufficiently stable for being further processed. In light of the foregoing, there is a need for an improved device and process for separating plasma from a whole blood sample.

SUMMARY OF THE INVENTION

The details of one or more embodiments of the invention are set forth in the accompanying drawings and the description below. Other features, objects, and advantages of the invention will be apparent from the drawings and detailed description, and from the claims.

Other and further objects, features and advantages of the invention will appear more fully from the following description. The accompanying drawings illustrate preferred embodiments of the invention, and together with the general description given above and the detailed description given below, serve to explain the principles of the invention.

BRIEF DESCRIPTION OF THE FIGURES

FIG. 7 depicts the embodiment in FIG. 6 as a schematic sectional view from the side.

DEFINITIONS

Figure 1:
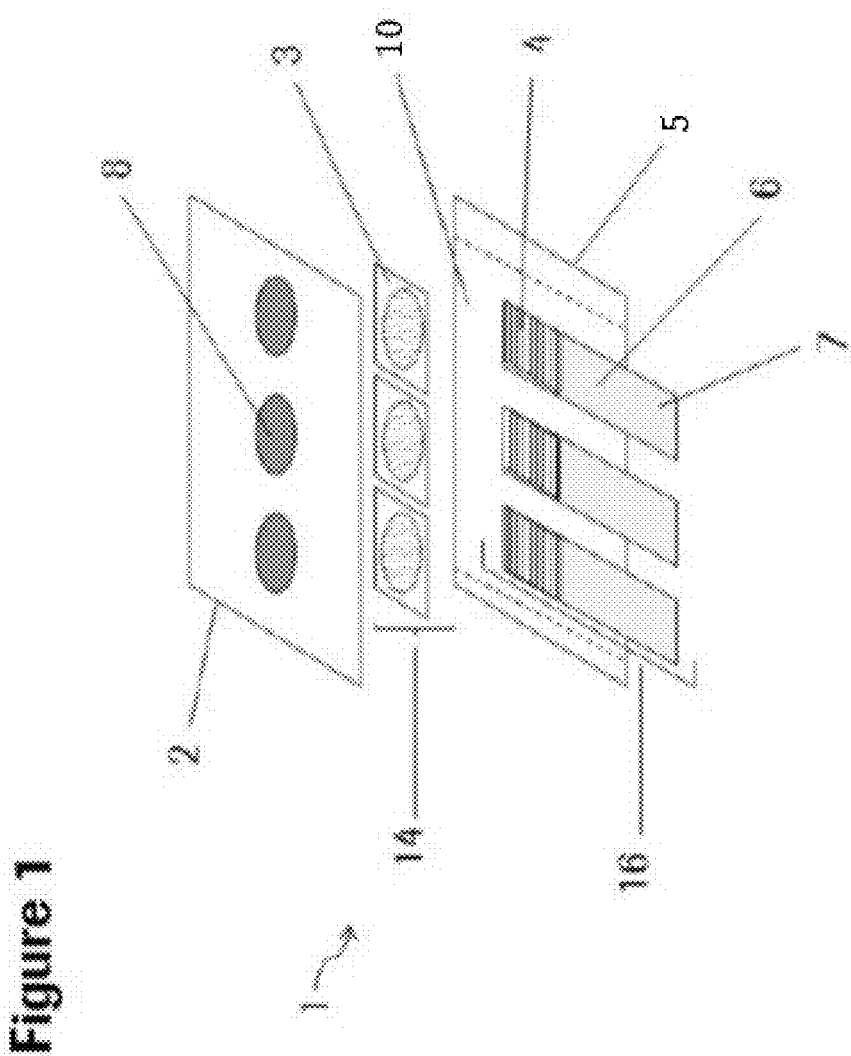
FIG. 1 shows a schematic exploded view illustrating an exemplary embodiment of the device according to the invention; 2: first layer (spotting layer) for applying or receiving blood sample, 3: membrane for separating plasma from whole blood, 4: absorptive element adapted to contact the bottom planar surface of one or more separating layers 3; 10: backing member or material to support the absorptive elements 4 or absorptive members 16; 6 and 7: first and second part extending absorptive element 4, wherein the second part 7 is free of any contact with any of the layers of the device, a so-called "handle"; 8: receiving portions on the first layer (spotting layer); 5: third layer comprising one or more removable absorptive members for collecting the plasma fraction; 14: second layer comprising one or more separation membranes; and 16: absorptive member comprising an absorptive element 4 and a first and second part 6,7 extending said absorptive element.

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The term "plasma separation" refers to separating plasma from a whole blood sample including a partial volume of plasma wherein substances, e.g., substances being characteristic of specific infection such as HIV particles, are detected, and a partial volume of cellular components (hematocrit).

The term "spotting layer" or "layer 2" refers to the top layer of the PSC consisting of a suitable film material having a thickness between approximately 100 and 400 µm preferably between 150 and 250 µm. Suitable materials for preparing the spotting layer are for example polyethylenterephthalate (PET) or related plastic materials.

The term "receiving member" refers to a first layer (usually the top or spotting layer) comprising one or more "sample receiving portions" or "receiving portions". The one or more sample receiving portions are adapted to permit contact of said blood sample with the separation layer. The sample receiving portion may be an opening, e.g., a substantially circular opening, with a three-dimensional domain that permits application of a blood sample and direct efficient distribution of the blood sample. In one embodiment, the sample receiving portion is a punched-out or laser-cut circular or oval hole. In another embodiment, the height of the side walls of the three-dimensional domain of each receiving portion is between 0.1 and 0.5 mm, preferably approximately 0.15 to 0.2 mm. The size of each of the sample receiving portions is usually smaller (e.g., approx. 10 mm diameter) than the size of each of the surfaces of the "separating member" or "absorptive member" of the following, the separation layer. In some embodiments, there are 2-6, preferable 2 or 3 of such receiving portions per PSC.

The term "separating member" refers to a second layer, the separation layer, made up of one or more plasma separation membrane regions allowing the efficient removal of the cellular components of whole blood applied to the openings at the spotting layer. Suitable plasma separation membranes are composed of, e.g., an asymmetric polysulfone material as for example membranes like the Vivid™ Membrane (available from Pall Corp., Port Washington, N.Y./USA). In general, asymmetric membranes having a shiny side and a dull (or rough) side are suitable. The dull side is the top surface, i.e., the surface to which a liquid sample is added. One separation member may preferably comprise a top planar shield-shaped surface for filtering plasma from a blood sample added through an opening (e.g., sample receiving portion), and a bottom planar shield-shaped surface being adapted to contact a third layer of the PSC. The shield-shaped surface of one or more separation members may be stamped, e.g., the frame or border region of the shield-shaped surface is sealed to a membrane resulting in a circular or nearly circular liquid-tight frame suitable to prevent or avoid leakage of liquid samples like blood. Sealing of the frame or border region can be achieved by applying mechanical forces, e.g., by compressing the membrane to approximately 30-40% of its original thickness, or by treating the surface of the membrane with a laser (the width of the resulting frame or border is 0.5 to 2.0 mm, preferably 0.8 to 1.2 mm). Applying thermal mechanical compressing or cutting results in a sealing wherein the width of the frame or border is 2.0 mm or less, preferably the cutting edge itself is used as a sealing with the consequence there is no frame or border area. The size of an area of the planar shield-shaped surface of one separation member is usually between 100 and 300 mm$^2$, preferably approximately 200 mm$^2$.

The term "absorptive member" refers to an area on a third layer adapted to the form of the bottom planar surface of one or more separating members of the second layer. The absorptive member may comprise a removable strip comprising an "absorptive element" having a top planar surface being adapted to contact to the bottom planar surface of the separating member and optionally a non-absorptive handle adjacent to the absorptive element. The non-absorptive handle supports removing the absorptive element. The absorptive member may take the form of a shield-shaped area comprising a removable absorptive element having a top planar shield-shaped. The absorptive element may comprise means for removable fixing the adsorptive element with the third layer, e.g., at least two elements functioning as connecting pieces or anchor elements for fixing the removable absorptive element to the third layer. The connecting pieces or anchor elements may comprise blocking or sealing elements. For example, hydrophobic or UV-glue treated blocking elements are suitable means to prevent or avoid leakage of liquid samples like plasma. The absorptive element may have a longitudinally folded two-dimensional structure or comprises a longitudinally folded planar area. One advantage of the adsorptive element having a longitudinally planar or two-dimensional structure is that the flow-through efficiency of the sample is increased. Another advantage of the absorptive element having a shield-shaped form and/or having a longitudinally folded planar or two-dimensional structure is that said element can be easily transferred into tubes for further processing, e.g., incubation and analysis. The absorptive member is preferably composed of a plasma collection fleece or material (e.g., a fleece consisting of cotton linters with an average thickness of 300-420 µm, a fleece used in Whatman™ 903™ paper, a fleece known as FP2992, FP2316 or ISP7216 which are available, e.g., from Hahnemühle GmbH, Dassel/Germany) or a plasma collection material which is not dissolvable in water or buffer containing solutions (e.g., a net, grid or membrane material, commercially available e.g. from Diomics Corp., San Diego, Calif./USA, or VWR International).

The term "backing member" refers to the area of the third layer outside the absorptive member arranged in a manner to support the absorptive members.

DETAILED DESCRIPTION OF THE INVENTION

By way of illustration, specific exemplary embodiments in which the invention may be practiced are described. With reference to FIGS. 1-10, by means of a schematic diagram, exemplary embodiments of the device for separating plasma from a whole blood sample are explained. Accordingly, a device for separating plasma from a whole blood sample generally referred to a reference numeral 1 includes a multi-layer plasma separation card format.

FIG. 1 depicts one embodiment of the plasma separation card (PSC) with multiple layers. The first layer 2 is for applying or receiving a blood sample. The first layer 2 has a top planar surface for applying or receiving a blood sample and a bottom planar surface adapted to contact a separating member 3. In one embodiment, the blood sample is applied to sample receiving portion 8. In another embodiment, the sample receiving portion 8 is adapted to permit contact of said blood sample with a separating member. For example, the sample receiving portion 8 may be an opening (e.g., a substantially circular opening) in the first layer 2 that permits application of a blood sample directly to a separating member 3. In one embodiment, the sample receiving portion 8 is a punched-out circular hole.

In one other embodiment, the PSC has a second layer 14 made up of two or more separating members 3. In other embodiments, the second layer 14 has at least two, three, four, or five separating members 3. The separation member 3 comprises a plasma separation membrane (e.g., Vivid™ Membrane). In one embodiment, the separation member 3 is an asymmetric membrane with two sides. For example, a Vivid™ Membrane has a shiny side and a dull (or rough) side. The dull side is the top surface, i.e., the surface to which a liquid sample will be added. In another embodiment, the separation member 3 comprises a top planar surface for filtering plasma, e.g., from a blood sample added through an opening (e.g., sample receiving portion 8) in the first layer 2, and a bottom planar surface being adapted to contact a third layer 5 of the PSC.

Figure 2:
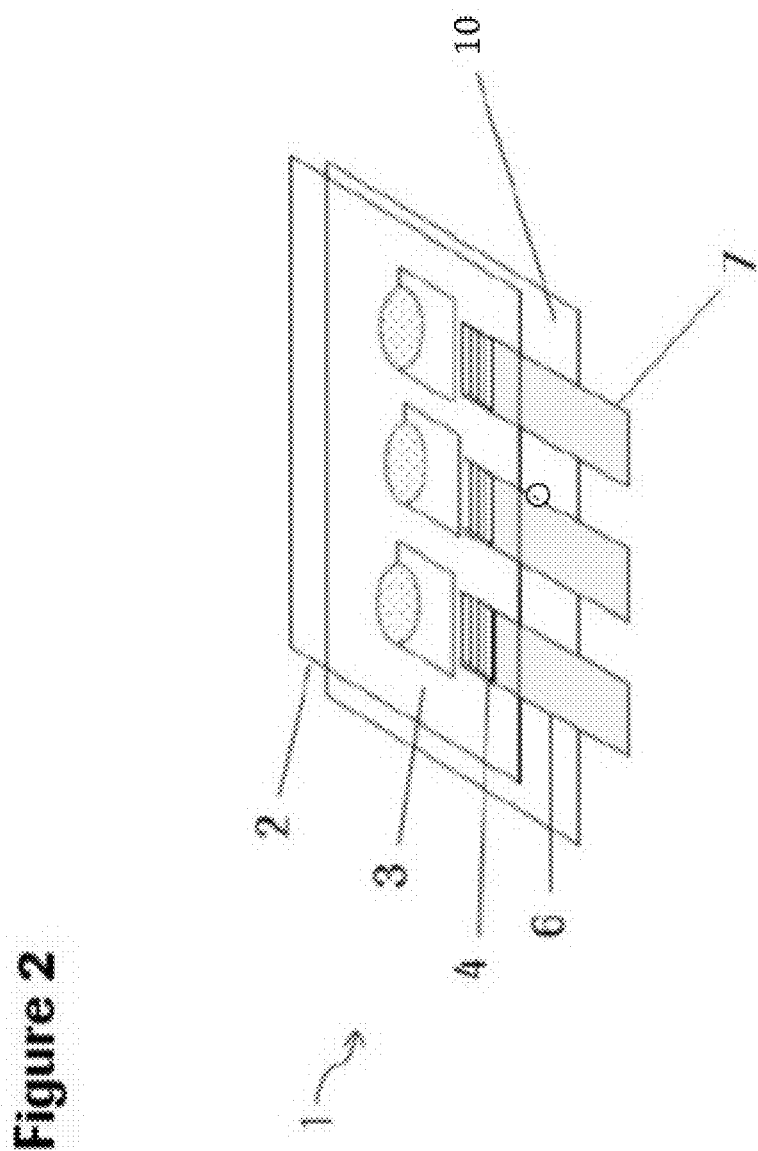
FIG. 2 depicts the embodiment in FIG. 1 in a layered format.
Figure 5:
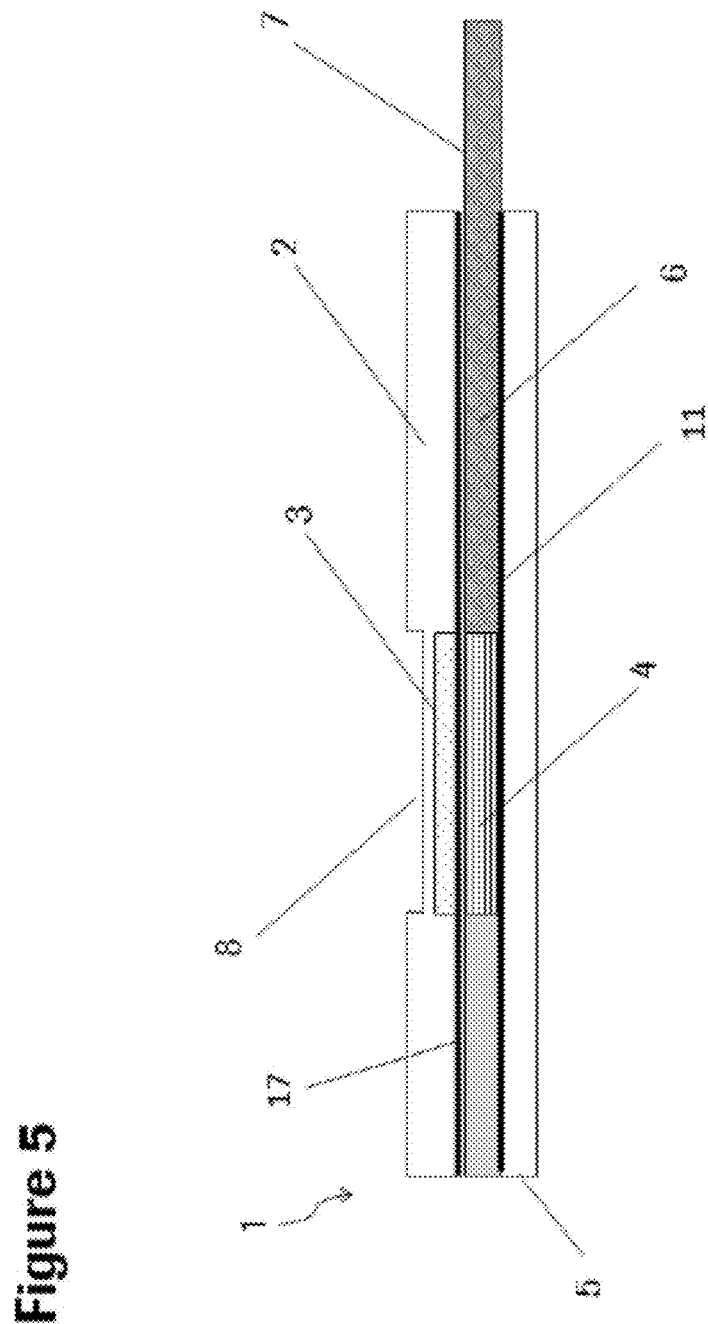
FIG. 5 depicts the embodiment of FIG. 2 as a schematic sectional view from the side.

In another embodiment, the PSC has a third layer 5 that contains two or more absorptive members 16 and a backing member 10 arranged in a manner to support the absorptive members 16. In some embodiments, the third layer 5 has at least two, three, four, or five absorptive members 16. The absorptive member 16 takes the form of a strip that comprises (i) an absorptive element or region 4 that is adapted to contact the bottom planar surface of one or more separation layers 3, and (ii) a non-absorptive element that is adjacent to the absorptive element 4 and is composed of a first part 6 and a second part 7. In one embodiment, first part 6 of the non-absorptive element is adapted to contact the bottom planar surface of one or more separation layers 3 and second part 7 of the non-absorptive element is adapted not to contact the bottom planar surface of one or more separation layers 3. The non-absorptive element means that the element does not absorb liquid, e.g., plasma or blood. In one embodiment, at least a portion of the second part 7 of the non-absorptive element is free of any contact with any or all of the following: the first layer 2, the second layer 14, and the third layer 5. This "free" configuration of the second part 7 is also illustrated in FIGS. 2 and 5.

In a preferred embodiment, the absorptive element or region 4 is composed of a plasma collection material (e.g., a Whatman™ 903™ card). In another embodiment, the absorptive element 4 comprises a plasma stabilizer.

In another aspect, the different layers of the plasma separation card are attached with a removable adhesive. In one embodiment, the adhesive is one that allows for the detachment of one PSC layer from another without causing substantial damage to any of the PSC layers. FIG. 5 illustrates an exemplary placement of such adhesives. In another embodiment, a removable adhesive 17 is used to attach the bottom planar surface of the first layer 2 to the top planar surface of one or more separating elements 3. In another embodiment, the removable adhesive 17 is positioned along the outer edges of the bottom planar surface of the first layer 2 of the card. In one embodiment, the removable adhesive 17 is positioned to superimpose over a separation element 3. In one other embodiment, the removable adhesive comprises holes corresponding to the punched-out holes in the first layer 2. In one additional embodiment, a removable adhesive is used to attach the bottom planar surface of each separating element 3 to the top planar surface of each absorptive member 4.

In another embodiment, the first layer 2 may be made of cardstock with a certain length and width (e.g., same length and width as the first area of the top surface of the third layer 5).

Figure 3:
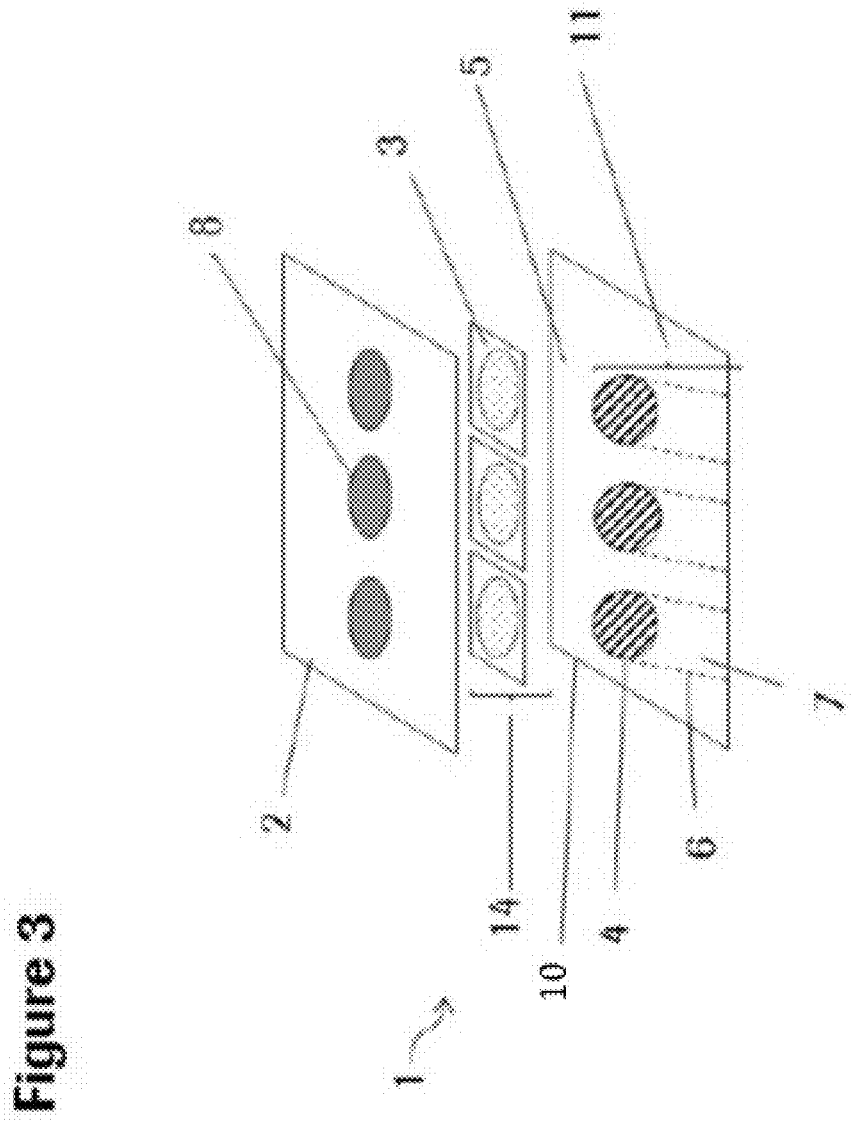
FIG. 3 shows a schematic sectional view illustrating another exemplary embodiment of the device according to the invention.

FIG. 2 depicts an assembled view of the plasma separation card (PSC) from FIG. 1. FIG. 3 depicts another embodiment of the PSC with multiple layers. The first layer 2 is for applying or receiving a blood sample. The first layer 2 has a top planar surface for applying or receiving a blood sample and a bottom planar surface adapted to contact a separating member 3. In one embodiment, the blood sample is applied to sample receiving portion 8. In another embodiment, the sample receiving portion 8 is adapted to permit contact of said blood sample with a separating member. For example, the sample receiving portion 8 may be an opening (e.g., a substantially circular opening) in the first layer 2 that permits application of a blood sample directly to a separating member 3.

In one other embodiment, the PSC has a second layer 14 made up of two or more separating members 3. In other embodiments, the second layer 14 has at least two, three, four, or five separating members 3. The separation layer is a plasma separation membrane (e.g., Vivid™ Membrane). In one embodiment, the separation member is an asymmetric membrane with two sides. For example, a Vivid™ Membrane has a shiny side and a dull (or rough) side. The dull side is the top surface, i.e., the surface to which a liquid sample will be added. In another embodiment, the separation member 3 comprises a top planar surface for filtering plasma, e.g., from a blood sample added through an opening in the first layer 2, and a bottom planar surface being adapted to contact an absorptive member.

In another embodiment, the PSC has a third layer 5 that contains two or more absorptive members 11 and a backing member 10 arranged in a manner to support the absorptive members 11. In some embodiments, the third layer 5 has at least two, three, four, or five absorptive members 11. The absorptive member 11 takes the form of a strip that can be removed from the third layer 5, wherein the strip comprises (i) an absorptive element or region 4 that is adapted to contact the bottom planar surface of one or more separation layers 3, and (ii) a handle that is adjacent to the absorptive element 4 and is composed of a first part 6 and a second part 7. In a preferred embodiment, the absorptive member 11 has a perforated border 6 which allows it to be removed from the third layer 5 without damaging the remaining part of the third layer 5 or another absorptive member 11.

In one embodiment, at least one separating element 3 is completely or partially superimposed over at least one absorptive element 4. In other embodiments, the first part 6 of the handle is adapted to contact the bottom planar surface of one or more separation layers 3 and at least a region of the second part 7 of the handle is adapted not to contact the bottom planar surface of one or more separation layers 3.

In other embodiments, the perforated border 6 extends to at least one edge of the third layer 5 (see FIG. 3).

In one embodiment, the absorptive member 11 comprises an absorptive element 4 adapted to absorb plasma through the bottom planar surface of a separation member 3, and a handle having second part 7 adjacent to first part 6. The second part 7 is adapted to be used to remove the absorptive member 11 from the third layer 5. For example, the second part 7 may be gripped, e.g., with tweezers, and used to pull the absorptive member 11 free along the perforated border 6. In a preferred embodiment, the absorptive element or region 4 is composed of a plasma collection material (e.g., a Whatman™ 903™ card). In other embodiments, the entirety of (i) the absorptive element 11 defined by the perforated border 6, and/or (ii) the third layer 5 is composed of a plasma collection material (e.g., a Whatman™ 903™ card). In another embodiment, the absorptive element 4 comprises a plasma stabilizer.

Figure 4:
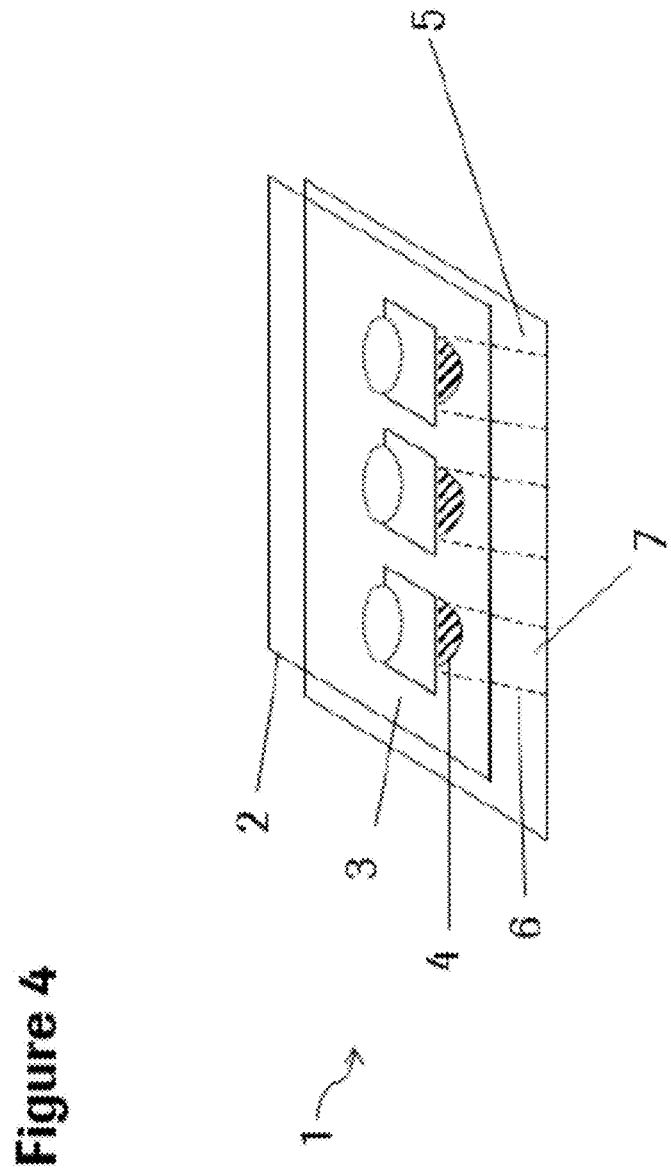
FIG. 4 depicts the embodiment in FIG. 3 in a layered format.

FIG. 4 depicts an assembled view of the PSC from FIG. 3.

In another aspect, the different layers of the plasma separation card are attached with a removable adhesive. In one embodiment, the adhesive is one that allows for the detachment of one PSC layer from another without causing substantial damage to any of the PSC layers. For example, FIG. 5 illustrates an exemplary placement of such a removable adhesive. In another embodiment, a removable adhesive 17 is used to attach the bottom planar surface of the first layer 2 to the top planar surface of one or more separating elements 3. In another embodiment, the removable adhesive 17 is positioned along the outer edges of the bottom planar surface of the first layer 2 of the card. In one embodiment, the removable adhesive 17 is positioned to superimpose over a separation element 3. In one other embodiment, the removable adhesive comprises holes corresponding to the punched-out holes in the first layer 2.

In another embodiment, the first layer 2 may be made of cardstock with a certain length and width (e.g., same length and width as the first area of the top surface of the third layer 5). In one additional embodiment, the top planar surface of the first layer 2 comprises one or more circular markings corresponding to each sample receiving portion 8.

Figure 6:
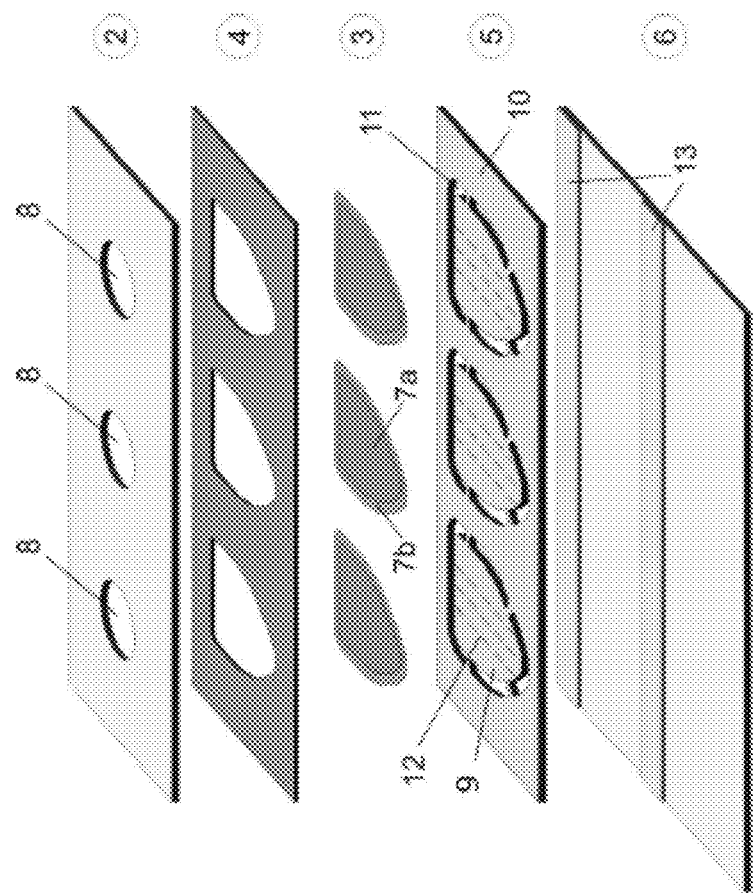
FIG. 6 shows a schematic exploded view illustrating another exemplary embodiment of the device according to the invention; 2: first layer (spotting layer) for applying or receiving blood sample, 3: membrane for separating plasma from whole blood, 4: intermediate layer comprising a double-sided adhesive material for blocking or limiting the distribution of blood, 5: third layer comprising one or more removable absorptive members for collecting the plasma fraction, 6: carrier layer for protecting and stabilizing the device comprising an adhesive material 13, 7a: second layer comprising one or more separation membranes, 7b: grouted or compressed frame or border to avoid leakage of the blood sample, 8: receiving portions on the first layer (spotting layer), 9: absorptive member comprising a removable absorptive element without or with anchor elements for fixing the removable absorptive element to the third layer, 10: backing member or material to support the absorptive members, 11: perforated border which allows to remove the absorptive member from the third layer, 12: longitudinally folded planar area on the absorptive member 9, and 13: adhesive material to fix and support the device.
Figure 8A:
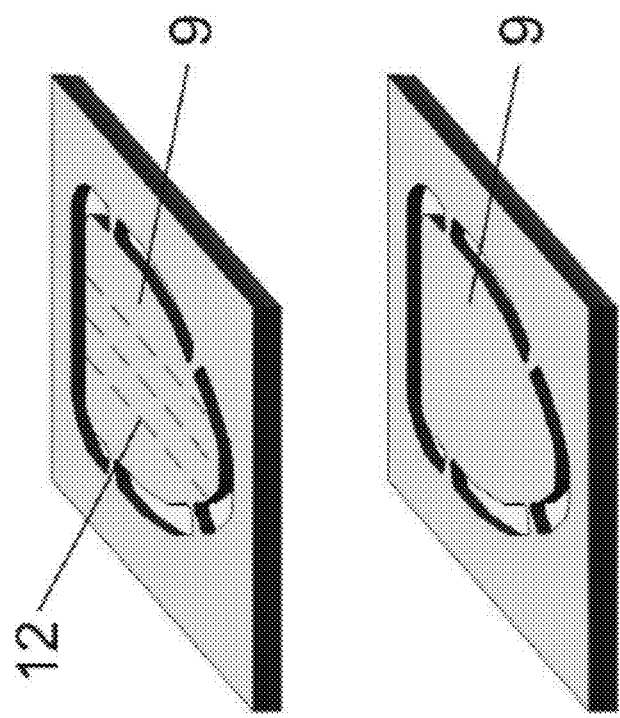
FIG. 8a, FIG. 8b, and FIG. 8c show a schematic sectional view where the shield-shaped area comprising the collection material including plasma is within or detached from the exemplary embodiment of the device according to the invention, (a) shows two types of absorptive members 9, one including a longitudinally folded planar area, 12, the other one with an unfolded even surface, (b) shows an embodiment wherein the anchor elements are comprising a blocking element, 14, to avoid leakage of the plasma sample from the collection material, (c) shows an absorptive member, 9, comprising a removable absorptive element with anchor elements, 16, or without anchor elements, 15.
Figure 8B:
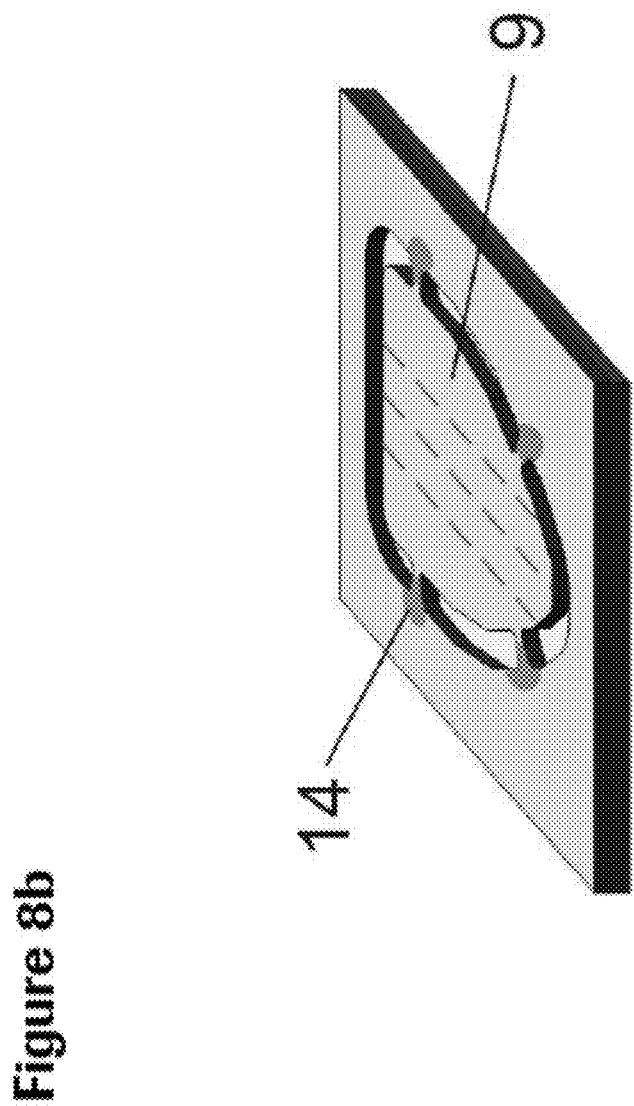
Figure 8C:
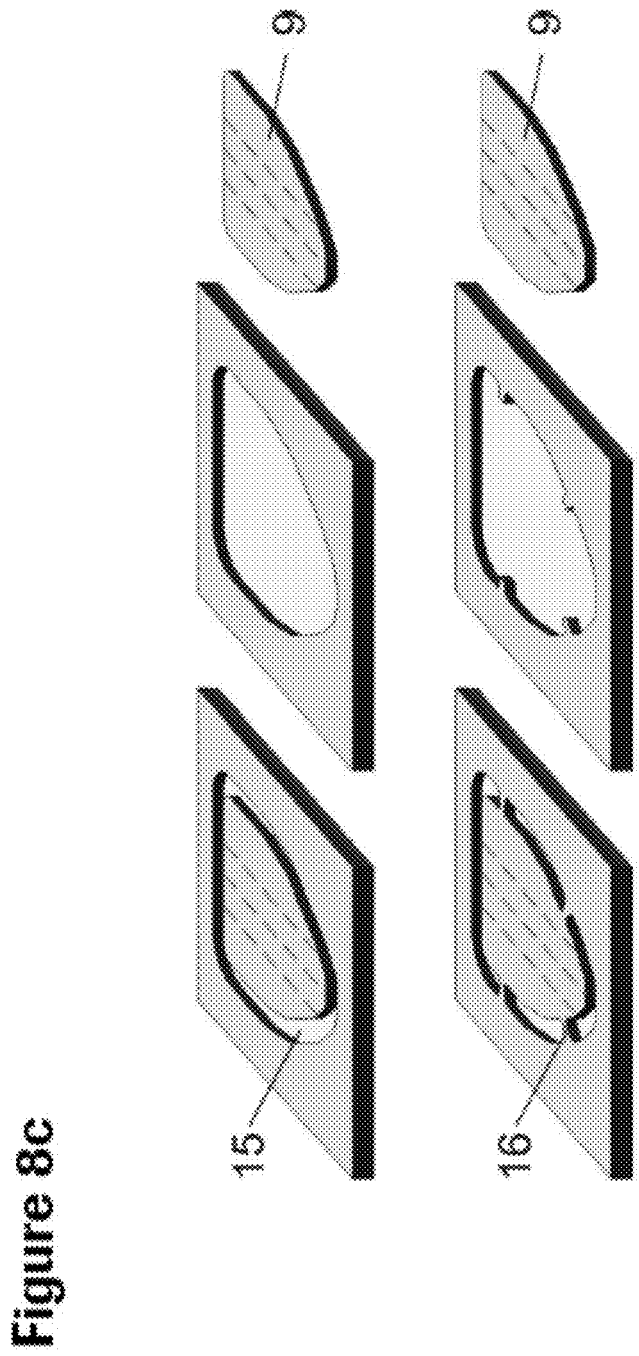

FIG. 6 depicts one embodiment of the plasma separation card (PSC) with multiple layers. The first layer 2 is for applying or receiving a blood sample (spotting layer). The first layer 2 has a top planar surface for applying or receiving a blood sample and a bottom planar surface adapted to contact a separating member 7. In one embodiment, the blood sample is applied to one or more sample receiving portions 8. The one or more sample receiving portions 8 are adapted to permit contact of said blood sample with one or more separating members 7, e.g., with the impact of capillary forces. For example, each of the sample receiving portions 8 may be an opening (e.g., a substantially circular opening) with a three-dimensional domain in the first layer 2 that permits application of a blood sample and direct efficient distribution of the blood sample to a separating member 7. In one embodiment, the sample receiving portion 8 is a punched-out circular or oval hole. In another embodiment, the height of the side walls of the three-dimensional domain of each receiving portion 8 is between 0.1 and 0.5 mm, preferably approximately 0.15 to 0.2 mm.

In one embodiment, the PSC has a second layer 3 made up of two or more separating members 7 (separation layer). In other embodiments, the second layer 3 comprises at least two, three, four, or five separating members 7. The separation layer 3 or separation member 7 comprises a plasma separation membrane allowing the efficient removal of the cellular components of whole blood. Suitable plasma separation membranes constructed of an asymmetric polysulfone material are for example membranes like the Vivid™ Membrane (available from Pall Corp., Port Washington, N.Y./ USA). In one embodiment, the separation layer 3 or separation member 7 is an asymmetric membrane with two sides. An asymmetric membrane, e.g., the Vivid™ Membrane, has a shiny side and a dull (or rough) side. The dull side is the top surface, i.e., the surface to which a liquid sample will be added. In another embodiment, the separation member 7 comprises a top planar shield-shaped surface for filtering plasma from a blood sample added through an opening (e.g., sample receiving portion 8) in the first layer 2, and a bottom planar shield-shaped surface being adapted to contact a third layer 5 of the PSC. In one other embodiment, the area of the planar shield-shaped surface of one separation member 7 is between 100 and 300 $mm^2$, preferably approximately 200 $mm^2$. The size of each of the sample receiving portions 8 is usually smaller (e.g., approx. 10 mm diameter) than the size of each of the surfaces of the separating member 7 or absorptive member (e.g., approx. 200 $mm^2$).

In a further embodiment the edges of the shield-shaped surface of one or more separation members are stamped. In one embodiment the frame or border region of the shield-shaped surface is sealed to a membrane resulting in a circular or nearly circular liquid-tight frame suitable to prevent or avoid leakage of liquid samples like blood.

Sealing of the frame or border region can be achieved by applying mechanical forces, e.g., by compressing the membrane to approximately 30-40% of its original thickness, or by treating the surface of the membrane with a laser (the width of the resulting frame or border is 0.5 to 2.0 mm, preferably 0.8 to 1.2 mm). Applying thermal mechanical compressing or cutting results in a sealing wherein the width of the frame or border is 2.0 mm or less, preferably the cutting edge itself is used as a sealing with the consequence there is no frame or border area.

A particular embodiment of the PSC comprises an intermediate layer or spacer layer 4 between the first layer 2 (spotting layer) and the second layer 3 (separating layer). Said spacer layer 4 comprises openings adapted to the sample receiving portions of the first layer 2 on the one hand and to the separating members 7 of the second layer 3 on the other hand. In one embodiment, the openings in the spacer layer 4 are punched-out holes adapted to the form of the planar shield-shaped surface of each of the one, two or more separating members 7 in the second layer 3. The spacer layer 4, for example, comprises an adhesive material, e.g., a double sided adhesive tape, having a thickness of 0.05 to 0.3 mm, preferably a thickness between 0.1 and 0.2 mm.

In another embodiment, the PSC has a third layer 5 that contains two or more absorptive members 9 and a backing member 10 arranged in a manner to support the absorptive members 9. In some embodiments, the third layer 5 has at least two, three, four, or five, in particular three absorptive members 9. Each absorptive member 9 takes the form of a shield-shaped area or a strip that comprises a removable absorptive element having a top planar shield-shaped surface that is adapted to contact the bottom planar surface of one or more separating members 7. The absorptive element comprises means for removable fixing the absorptive element with the third layer 5. In one embodiment the removable absorptive element comprises at least two elements for fixing the removable absorptive element with the third layer 5. In one other embodiment, the removable absorptive element is adapted to avoid or reduce the formation of air bubbles, e.g., the absorptive element has a longitudinally folded two-dimensional structure or comprises a longitudinally folded planar area. A further advantage of the absorptive element having a longitudinally planar or two-dimensional structure is that the flow-through efficiency of the sample is increased. Another advantage of the absorptive element having a shield-shaped form and/or having a longitudinally folded planar or two-dimensional structure is that said element can be easily transferred into tubes for further processing, e.g., incubation and analysis.

In one particular embodiment, the removable absorptive element of the absorptive member 9 is composed of a plasma collection fleece or material (e.g., a fleece consisting of cotton linters with an average thickness of 300-420 µm, a fleece used in Whatman™ 903™ paper, appropriate fleece materials, e.g., FP2992, FP2316 or ISP7216 are available, e.g., from Hahnemühle GmbH, Dassel/Germany). In another embodiment, the absorptive element is composed of a plasma collection material which is not dissolvable in water or buffer containing solutions (e.g., a net, grid or membrane material, commercially available e.g. from Diomics Corp., San Diego, Calif./USA, or VWR International). In a further embodiment, the absorptive element of the absorptive member 9 comprises a plasma stabilizer.

Figure 9:
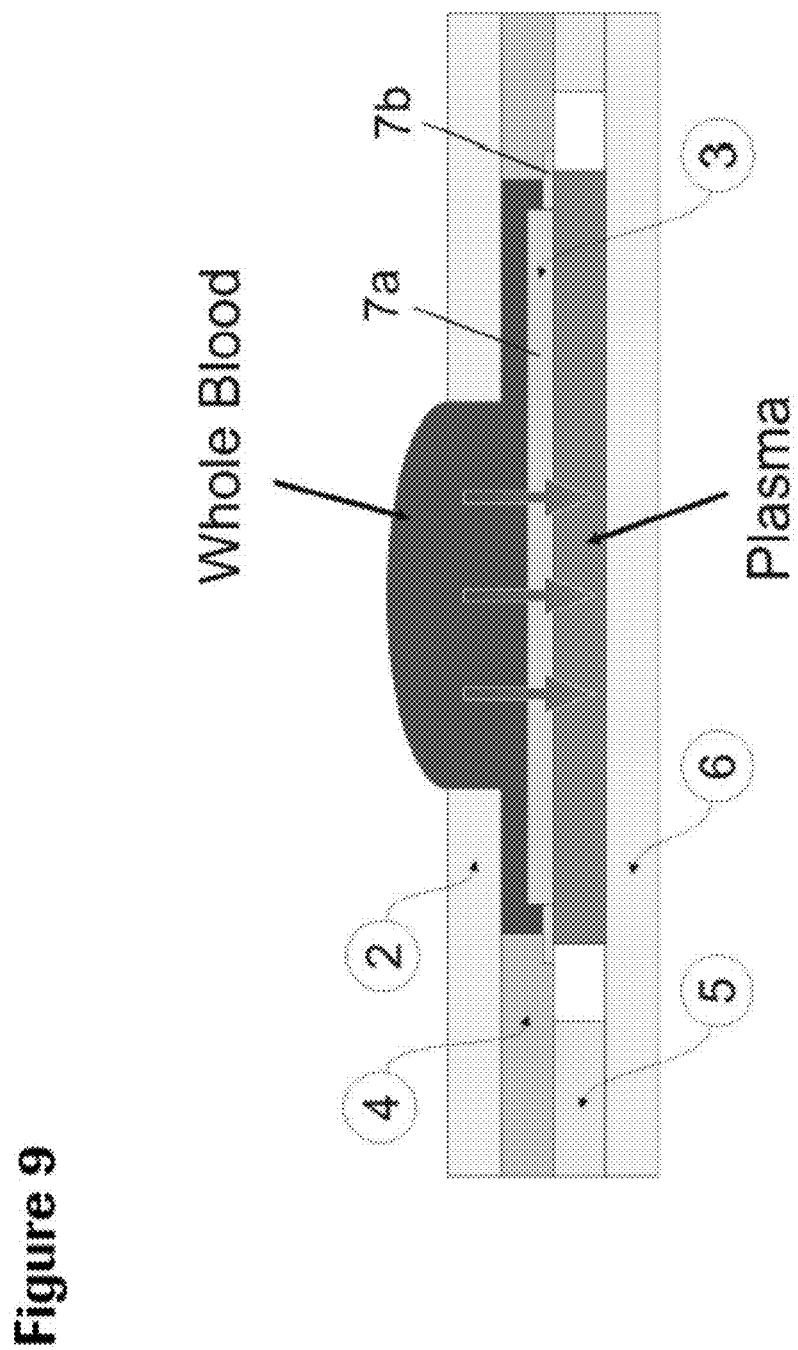
FIG. 9 depicts the embodiment in FIG. 6 with applied whole blood sample as a schematic sectional view from the side. A whole blood sample is applied on the receiving member of the spotting layer. The blood sample is distributed through the opening of the device to the absorptive member comprising a plasma collection material via capillary forces.

In another aspect, the different layers of the plasma separation card are attached with a removable adhesive. In one embodiment, the adhesive is a means that allows the detachment of one PSC layer from another layer without causing substantial damage to any of the PSC layers. Each of FIGS. 6, 7 and 9 illustrates an exemplary placement of such adhesives. In another embodiment, a removable adhesive 4 is used to attach the bottom planar surface of the first layer 2 to the top planar surface of one or more separating members 7. In another embodiment, the removable adhesive 4 is positioned along the outer edges of the bottom planar surface of the first layer 2 of the card. In one embodiment, the removable adhesive 4 is positioned to superimpose over a separation member 7. In one other embodiment, the removable adhesive 4 comprises openings corresponding to the punched-out holes in the first layer 2. In one additional embodiment, a removable adhesive is used to attach the bottom planar surface of each separation member 7 to the top planar surface of each absorptive member 9.

In another embodiment, the first layer 2 may be made of cardstock with a certain length and width (e.g., same length and width as the first area of the top surface of the third layer 5).

FIGS. 7 and 9 each depicts the embodiment of the PSC from FIG. 6 as a schematic sectional view from the side.

In one other embodiment, the PSC has a second layer 3 made up of two or more separating members 7 (separation layer). In other embodiments, the second layer 3 has at least two, preferably three separating members 7. The separation layer is a plasma separation membrane (e.g., an asymmetric membrane based on polysulfone, a Vivid™ Membrane). In one embodiment, the separation member is an asymmetric membrane with two different sides. For example, a Vivid™ Membrane has a shiny side and a dull (or rough) side. The dull side is the top surface, i.e., the surface to which a liquid sample will be added. In another embodiment, the separation member 7 comprises a top planar shield-shaped surface for filtering plasma, e.g., from a blood sample added through an opening in the first layer 2, and a bottom planar shield-shaped surface being adapted to contact an absorptive member 9.

In another embodiment, the PSC has a third layer 5 that contains two or more absorptive members 9 and a backing member 10 arranged in a manner to support the absorptive members 9. In some embodiments, the third layer 5 has at least two, preferably three absorptive members 9. Each absorptive member 9 takes the form of a shield-shaped area that comprises a removable absorptive element having a top planar shield-shaped surface that is adapted to contact the bottom planar surface of one or more separation layers. In a preferred embodiment, the absorptive member 9 has a perforated border 11 which allows it to be removed from the third layer 5 without damaging the remaining part of the third layer 5 or another absorptive member 9.

In other embodiments, the perforated border 11 extends to at least one edge of the third layer 5 (see FIG. 6).

In one embodiment, the absorptive member 9 comprises an absorptive element adapted to absorb plasma through the bottom planar surface of a separation member 7 driven by the impact of capillary forces. In a preferred embodiment, the absorptive element is composed of a plasma collection material having a sucking capacity of at least 150 g/m$^2$, preferably a sucking capacity of 200-400 g/m$^2$ (e.g., a fleece consisting of cotton linters with an average thickness of 300-420 µm, a fleece used in Whatman™ 903™ paper, a fleece known as FP2992, FP2316 or ISP7216 which are available, e.g., from Hahnemühle GmbH, Dassel/Germany). In other embodiments, the (i) the absorptive element covered on each of the absorptive members 9, and/or (ii) the third layer 5 is composed of a plasma collection material (e.g., one of those mentioned above). In another embodiment, the absorptive element comprises a substance or mixture for stabilizing plasma.

In another aspect, the different layers of the plasma separation card are attached with a removable adhesive material. In one embodiment, the adhesive material is one that allows for the detachment of one PSC layer from another without causing substantial damage to any of the PSC layers. In a further embodiment the removable absorptive material or element comprises at least two elements for fixing the absorptive element with the third layer. In some embodiments the removable absorptive element comprises 3, 4 or 5 for fixing said element with the third layer.

FIG. 6 illustrates exemplary placements of such a removable adhesive, 4 and 13. In one embodiment, a removable adhesive is used to attach the bottom planar surface of the first layer 2 to the top planar surface of one or more separating members 7. In another embodiment, the removable adhesive is positioned along the outer edges of the bottom planar surface of the first layer 2 of the card. In one embodiment, the removable adhesive is positioned to superimpose over a separation member 7. In one other embodiment, the removable adhesive comprises holes corresponding to the punched-out holes in the first layer 2. In a further embodiment, a removable adhesive is positioned on the fourth layer. The fourth layer 6 serves as carrier supporting and stabilizing the plasma separation card. In a particular embodiment, the removable adhesive is positioned at each of the long edge sides of the support layer or carrier 6. The carrier 6 may consist of a stiff material as for example a strong paper or a film having a thickness of 350 µm and consisting of polyethylen-terephthalate, e.g., HOSTAPHAN® RN350.MED. Alternatively, a coated film with a activatable sticking layer, e.g., a film consisting of a polystyrene with a thickness range of approximately 100-400 µm, e.g., 350 µm, coated with an activatable adhesive or sticking layer may be used. The sticking layer might be thermally activated, e.g., welded by ultrasound or activated by pressure. The carrier might be fixed, wherein the fleece layer is only selectively welded outside the plasma reservoir signs. Thus, the "adhesive stripes 13" are omitted.

In one embodiment, the PSC comprises an additional layer, a so-called plasma level control layer, between said third layer 5 and the carrier or support layer 6. The plasma level control layer comprising a plasma level control substance is either directly in contact with or positioned adjacent to the removable absorptive material (e.g., fleece) for collecting the plasma fraction. In another embodiment, the support layer 6 (carrier) and the plasma level control layer are both transparent. PH indicators, e.g., Bromothymol Blue, or pH independent water sensitive papers (e.g., commercially available from Quantifoil Instruments GmbH, Jena/Germany) are suitable as plasma level control substances. If a pH indicator is used, the addition of plasma shifts the pH value towards the alkaline area triggering a color change. If a plasma level control layer comprising a water sensitive paper is used, the addition of plasma changes the color of the paper; the result is visible after a few seconds. The plasma level control layer in particular guarantees that enough plasma is present for the test and, further, ensures consistency of test results, given that constant amounts of starting materials are applied.

In another embodiment, the first layer 2 may be made of card stock with a certain length and width (e.g., same length and width as the first area of the top surface of the third layer 5). In one additional embodiment, the top planar surface of the first layer 2 comprises one or more circular markings corresponding to each sample receiving portion 8.

A preferred multi-layer plasma separation card according to the present invention comprises
(a) a first layer including a sample receiving member comprising (i) a top planar surface framed by a barrier element for applying or receiving a blood sample, said sample receiving portion being adapted to permit contact of said blood sample with a separating member through capillary forces; and (ii) a bottom planar surface being adapted to contact said separating member,
(b) a second layer including at least two separating members, each separating member being adapted to permit the passage of plasma to an absorptive member and comprising (i) a top planar shield-shaped surface for receiving said blood sample; and (ii) a bottom planar shield-shaped surface being adapted to contact said absorptive member, and
(c) a third layer including at least two absorptive members for absorbing plasma from the bottom planar shield-shaped surface of each corresponding separating member and a backing member arranged in a manner to support said absorptive members, each absorptive member comprising a removable absorptive element having a top planar shield-shaped surface being adapted to contact said bottom planar shield-shaped surface of the separating member, said absorptive element is removable fixed to the third layer.

In one embodiment, the multi-layer plasma separation card comprises a third layer, wherein the absorptive element comprises at least two elements for fixing the removable absorptive element with said third layer. In another embodiment, the multi-layer plasma separation card comprises a plasma level control layer linked to the third layer.

In one embodiment, the multi-layer plasma separation card comprises sample receiving portions wherein each of said sample receiving portions is a punched-out circular or oval hole. In another embodiment, the size of each of the sample receiving portions is smaller (e.g., approx. 10 mm diameter) than the size of each of the shield-shaped surfaces of the separating member or absorptive member (e.g., 200 $mm^2$). In a further embodiment, on each of the sample receiving portions 10 µl to 1000 µl, preferably 50 µl to 500 µl, more preferably 100 µl of a whole blood sample are applied. In one embodiment, one or more of the separating members comprises a plasma separation membrane (e.g., Vivid Membrane). In another embodiment of the multi-layer plasma separation card, the absorptive member is composed of a plasma collection material (e.g., a fleece consisting of cotton linters with an average thickness of 300-420 µm, a fleece used in Whatman™ 903™ paper, appropriate fleece materials, e.g., FP2992, FP2316 or ISP7216, are available, e.g., from Hahnemühle GmbH, Dassel/Germany) and optionally comprises a plasma stabilizer. In a preferred embodiment, each of the absorptive elements comprises a longitudinally folded planar area. In another preferred embodiment, the absorptive elements can be easily removed or transferred to a vessel for determination, e.g., with a tweezers.

A further object of the invention is a method for preparing a multi-layer plasma separation card, comprising steps (1) preparing a separation member layer, an absorptive member layer comprising a plasma separation fleece, a spotting layer and an adhesive layer, (2) combining the layers prepared by sticking the spotting layer onto the adhesive layer in a suitable device, wherein the separation membrane layer is inserted and grouted with the side of the adhesive layer not stuck to the spotting layer and subsequently putting the absorptive membrane layer onto the separation membrane layer and (3) sticking the composite of the layers onto a carrier support layer in longitudinal direction.

In one embodiment, the method for preparing a multi-layer plasma separation card, comprises the following steps (1) preparing one or more separation membranes (e.g. an asymmetric membrane prepared from polysulfone, a Vivid™ Membrane) in the desired form, e.g., in the form of shield-shaped areas, by mechanical punching or laser cutting, compressing with mechanical and/or thermal forces the frame and border region to approximately ⅓ of the original thickness of the membrane resulting in a circular frame with a breath of approximately 1 mm, (2) preparing the absorptive member layer comprising a plasma collection fleece on a backing material in the desired form by mechanical punching or laser cutting, wherein the longitudinally folded area or notches are embossed on the plasma collection fleece area with a press. Alternatively, the folding and creasing can be performed by applying ultrasonic or Kiss-cut technologies.

(3) preparing the spotting layer based on card stock paper with one or more holes or portions for applying blood samples by cutting and/or punching, (4) preparing a layer consisting of a double-sided adhesive material comprising holes or openings corresponding to the punched-out holes of the spotting layer (3) and adapted to the form of the one or more separation membranes (1), (5) preparing a carrier support layer comprising a double-sided adhesive material positioned at each of the long sides of the support layer, and (6) combining the layers obtained by steps (1) to (5) as follows: Sticking the spotting layer derived from step (3) onto the adhesive layer derived from step (4) in a suitable device wherein the separation membrane derived from step (1) is inserted and grouted with the side of the adhesive layer not stuck to the spotting layer and subsequently putting the fleece layer derived from step (2) onto the separation membrane. The composite of the layers derived from steps (1) to (4) is then stuck to a carrier support layer in longitudinal direction.

The present invention is further directed to a packaging concept for supplying a multi-layer plasma separation card. In one embodiment, the packaging concept comprises an impermeable, moisture-resistant, chemically inert bag, e.g. prepared from aluminum foil or aluminum coated plastic film, comprising a multi-layer separation card and a drying agent or a desiccant (single-card packaging). The bag with a size essentially adapted to the size of the multi-layer plasma separation card comprising the plasma separation card and, e.g., the desiccant is usually hermetically sealed until it is opened for use. In an advantageous embodiment, the packaging concept further comprises a second impermeable, chemically inert closable bag for inserting and transporting the multi-layer plasma separation after use (that means including plasma sample(s)) and optionally means for taking of blood samples. Suitable means for taking blood samples are for example disposables like lancets. The shelf life of the unused multi-layer separation card provided with the packaging concept is at least 24 months, at a temperature of 18-45° C. and a relative humidity up to 85%. The plasma sample situated on the multi-layer separation card contained in a closed impermeable, chemically inert bag is stable for at least 12 weeks, at a temperature of 18-45° C. and a relative humidity up to 85%.

Another object of the invention is a method for detecting HIV, HCV and/or HBV in a plasma sample comprising using a multi-layer plasma separation card according to the invention.

EXAMPLES

Example 1: Preparation of the Multi-Layer Plasma Separation Card

The spotting Layer 2 consists of a 350 μm thick film made from stiff polyethylen-terephthalate (PET) material, commercially available as HOSTAPHAN® RN350.MED. From the material, usually supplied on rolls, multiple strips are cut in size of approximately 85×30 mm. Three holes 8 are cut out with a punch. The spacer 4 is made of a double-sided tape, e.g., tesafix 51570 or tesafix 4959 (commercially available from Tesa SE, Hamburg/Germany), having a thickness of ca. 0.1 mm, which is protected on both sides with a removable film. Multiple strips are cut out from the material supplied on rolls, wherein each strip is approximately 85×30 mm in size.

The three shield-formed openings are cut out with a laser. As membrane 3 has been used Vivid membrane GR (8"×11" sheet with a thickness of 0.3 mm; Pall Corp., Port Washington, N.Y./USA). Shield-shaped parts having an approximate size of 17×21 mm are punched out of a fleece 5 (e.g., cotton linters having an average thickness of 300-420 μm and a sucking capacity of 235-290 g/m$^2$), 7a. The edge 7b may be 1-2 mm wide and is pressed with a press to 0.1 mm. A comparable result can also be reached with laser or ultrasound means. As fleece material cotton linters, e.g., comprising a small amount of a polyamide-epichlorohydrin resin, having an average thickness of 300-420 μm and a sucking capacity of 235-290 g/m$^2$ was used. Other fleece materials having a thickness of 300-450 μm and a sucking capacity of 200-400 g/m$^2$ (e.g., FP2992, FP2316 or ISP7216 fleece, e.g., commercially available from Hahnemühle GmbH, Dassel/Germany) can also be used. Multiple strips with a size of approximately 85×30 mm were cut out the fleece material available in rolls.

Three spots 9 were produced from each of these stripes by using a laser. This step can also be performed by using a mechanical punch. The notches are embossed on the shield-formed area 9 with a press. This step can also be performed by using a laser, ultrasonic, or kiss-cut technologies. The carrier 6 may consist of a film having a thickness of 350 μm and consisting of polyethylen-terephthalate, e.g., HOSTAPHAN® RN350.MED. Cards of a size of approximately 85×53 mm are cut of the film material. In some embodiments, two double-sided adhesive stripes 13 might be adhered on the carrier cards in the longitudinal direction.

For the following steps means and devices for ensuring an accurate set-up are used. The protection film is removed from the double-sided adhesive material 4. The adhesive material was then applied flush fitting to the spotting layer 2. The second protection film was removed from the double-sided adhesive material 4, and the composition consisting of the spotting layer 2 and the spacer 4 were inserted into a device.

The Vivid membrane is inserted into a further device and glued or fixed on the spacer layer 4 linked to the spotting layer 2. This process has been repeated three times until all three spots were made. The layer comprising the plasma collection fleece is inserted into a still further device and glued by pick and place on the Vivid membrane layer of the composition consisting of spotting layer, spacer layer and the Vivid membrane. The protection film is removed from the adhesive tape(s) 13 and the composition consisting of the spotting layer, the spacer layer, the Vivid membrane and the plasma collection fleece is applied flush to the top of the carrier 6.

Example 2: Detection of HIV in a Plasma Sample Using the Multi-Layer Plasma Separation Card (PSC)

Experimental Workflow
1) An amount of whole blood (~100 ul) is applied onto one of the receiving members of the Plasma Separation Card (Spotting Layer).
2) The card is dried for 3-4 hours at room temperature.

3) After drying, the spotting layer with the attached membrane is peeled from the carrier. Tweezers are used to remove the one or more plasma filled shield-shaped areas (member 9 in FIG. 8a-c) and to transfer it/them into an appropriate sample tube(s).
4) 1100 μl of a Specimen Pre-Extraction (SPEX) buffer reagent is added to one tube each and the sample(s) is (are) incubated at 56° C. for 10-20 minutes with shaking at 1000 rpm.
5) Transfer of the tube(s) including the plasma sample(s) onto the instrument.
6) Starting of workflow on the instrument and measured.

In Table 1 the estimated Limit of Detection of the PSC in combination with the COBAS® AmpliPrep/COBAS® TaqMan® HIV Test, v2.0 and the CAP/CTM System and estimated Limit of Detection of the PSC in combination with the Cobas 4800 HIV Test and the Cobas® 4800 system is shown. The Limit of Detection and the corresponding confidence interval were calculated with 95% by using an established statistical method (Probit Analysis).

TABLE 1

| | | Limit of Detection | | |
|---|---|---|---|---|
| Platform | Sample | HIV | HBV | HCV |
| c4800 | Spiked Whole Blood | 613 cp/ml (CI: 601-1696) | 148 IU/ml (CI: 75-958) | 467 IU/ml (CI: 260 -2355) |
| CAP/CTM | Spiked Whole Blood | 502 cp/ml (CI: 340-1084) | 188 IU/ml (CI: 108-793) | N/A |

CI: Confidence Interval 95%

In Table 2 the estimated linearity of the PSC in combination with the Cobas® HIV and the Cobas® 6800/8800 system and the COBAS® AmpliPrep/COBAS® TaqMan® HIV Test, v2.0 and the CAP/CTM System is shown. Linearity was assessed using the predominant genotype HIV-1 Group M Subtype B in whole blood. The linearity panel was prepared as a serial dilution of a high titer cell culture supernatant covering the intended linear range. The resulting data were analyzed to identify the linear range according to Clinical and Laboratory Standard Institute (CLSI) guideline EP6-A. The linear range and the $R^2$ value were calculated.

TABLE 2

| | Linearity | | |
|---|---|---|---|
| Platform | HIV1 Concentration Levels | Sample | Linear Range |
| CAP/CTM | 200 cp/ml 400 cp/ml 1.0E3 cp/ml 1.0E4 cp/ml 1.0E5 cp/ml 1.0E7 cp/ml 2.0E7 cp/ml | HIV Spiked Whole Blood | Linearity is given over the range 400 – 2E+07 cp/ml $R^2 = 0.98$ |
| c6800 | 200 cp/ml 400 cp/ml 1.0E3 cp/ml 1.0E4 cp/ml 1.0E5 cp/ml 1.0E7 cp/ml 2.0E7 cp/ml | HIV Spiked Whole Blood | Linearity is given over the range 1000 – 2E+07 cp/ml $R^2 = 0.99$ |

Figure 10:
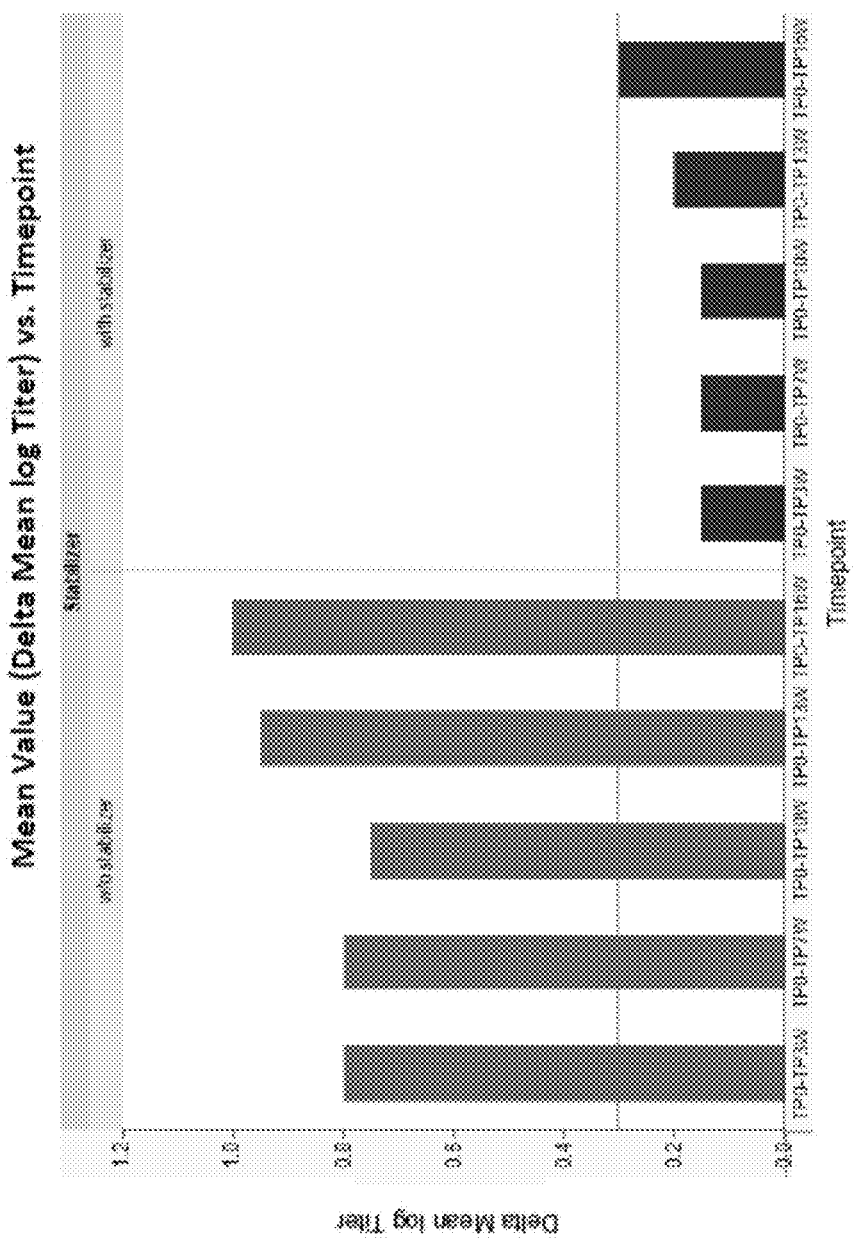
FIG. 10 shows the data in accordance to specimen stability testing over 16 weeks as described in Example 2 (Delta Mean log Titer v. Time point). A delta mean log titer value of the target of less or equal than 0.3 log cp/ml relative to time point zero at the start of the experiment (TP0) was defined as stability requirement. For example TP0-TP3W describes the relative delta mean log titer value after 3 weeks of storage.

In the diagram presented in FIG. 10 the data in accordance to specimen stability testing over 16 weeks is shown. A concentration of 1200 cp/ml was tested over a time period of 16 weeks at an elevated temperature of 40° C. and a relative humidity of 10-40%. A delta mean log titer value of the target of less or equal than 0.3 log cp/ml relative to time point zero at the start of the experiment (TP0) was defined as stability requirement. For example, TP0-TP3W describes the relative delta mean log titer value after 3 weeks of storage and the described conditions. Data with and without stabilizer is shown.

The invention claimed is:

1. A method for separating plasma from a whole blood sample, the method comprising:
    (1) providing a multi-layer plasma separation card, wherein the multi-layer plasma separation card comprises:
        (a) a first layer including a sample receiving member, wherein the sample receiving member is adapted to permit contact of the whole blood sample with a separating membrane, and wherein the sample receiving member comprises: (i) a top planar surface, wherein the top planar surface comprises an opening for applying or receiving a whole blood sample, and (ii) a bottom planar surface adapted to contact the separating member,
        (b) a second layer including at least two separating members, wherein each separating member is adapted to permit the passage of plasma to an absorptive member, wherein each separating member is composed of a poly-sulfone material, and wherein each separating membrane comprises: (i) a top planar shield-shaped surface for receiving the blood sample; and (ii) a bottom planar shield-shaped surface adapted to contact the absorptive member, and
        (c) a third layer including at least two absorptive members for absorbing plasma from the bottom planar surface of each corresponding separating member and a backing member arranged in a manner to support the absorptive members, wherein each absorptive member is composed of a plasma collection fleece or material, or a plasma collection material that is not dissolvable in water or buffer containing solutions, wherein each absorptive member comprises a removable absorptive element having a planar surface-adapted to contact the bottom planar surface of the separating member, wherein the absorptive element is detachably fixed to the third layer;
    (2) applying a whole blood sample onto the sample receiving member of the first layer; and
    (3) allowing components of the whole blood sample to pass through the first layer, second layer, and third layer of the multi-layer plasma separation card, such that the plasma is separated from the other components of the whole blood sample and is absorbed onto the absorptive element of the third layer.

2. The method of claim 1, wherein the at least two absorptive members are part of a strip, wherein the strip further comprises a non-absorptive handle adjacent to the absorptive element.

3. The method of claim 1, wherein the at least two absorptive members comprise at least two elements for fixing the removable absorptive element with the third layer.

4. The method of claim 1, wherein the size of each of the sample receiving portions is smaller than the size of each of the surfaces of the separating member or absorptive member.

5. The method of claim 1, wherein the whole blood sample applied onto the sample receiving member of the first layer in step (2) has a volume of between 10 μl to 1000 μl.

6. The method of claim 1, wherein the absorptive member comprises a fleece consisting of cotton linters with an average thickness of 300-420 μm.

7. The method of claim 1, wherein the absorptive members have perforated borders.

8. The method of claim 5, wherein the whole blood sample applied onto the sample receiving member of the first layer in step (2) has a volume of between 100 μl to 1000 μl.

9. The method of claim 1, wherein steps (1)-(3) are performed over the course of 3-4 hours.

10. The method of claim 1, further comprising the additional step of: (4) drying the multi-layer plasma separation card.

11. The method of claim 10, wherein during steps (1)-(3), the multi-layer plasma separation card is allowed to dry over the course of 3-4 hours.

12. The method of claim 7, wherein the absorptive members having perforated borders allow for easy removal and/or transferring of the absorptive elements to a vessel using tweezers.

\* \* \* \* \*